US009278453B2

(12) United States Patent
Assad

(10) Patent No.: US 9,278,453 B2
(45) Date of Patent: Mar. 8, 2016

(54) BIOSLEEVE HUMAN-MACHINE INTERFACE

(71) Applicant: Christopher Assad, Long Beach, CA (US)

(72) Inventor: Christopher Assad, Long Beach, CA (US)

(73) Assignee: California Institute of Technology, Pasadena, CA (US)

( * ) Notice: Subject to any disclaimer, the term of this patent is extended or adjusted under 35 U.S.C. 154(b) by 94 days.

(21) Appl. No.: 13/903,781

(22) Filed: May 28, 2013

(65) Prior Publication Data

US 2013/0317648 A1     Nov. 28, 2013

Related U.S. Application Data

(60) Provisional application No. 61/651,728, filed on May 25, 2012.

(51) Int. Cl.

| | |
|---|---|
| *B25J 9/16* | (2006.01) |
| *G06F 3/01* | (2006.01) |
| *B25J 9/10* | (2006.01) |
| *A61B 5/0488* | (2006.01) |
| *A61B 5/00* | (2006.01) |
| *A61B 5/11* | (2006.01) |
| *G06K 9/00* | (2006.01) |

(52) U.S. Cl.
CPC ........... *B25J 9/1694* (2013.01); *A61B 5/04888* (2013.01); *B25J 9/104* (2013.01); *G06F 3/011* (2013.01); *G06F 3/014* (2013.01); *A61B 5/1116* (2013.01); *A61B 5/1122* (2013.01); *A61B 5/6825* (2013.01); *A61B 5/6826* (2013.01); *A61B 5/6831* (2013.01); *A61B 5/721* (2013.01); *A61B 5/7267* (2013.01); *G05B 2219/36435* (2013.01); *G06K 9/00355* (2013.01)

(58) Field of Classification Search
CPC .......... B25J 9/1694; G06F 3/01; G06F 3/011; G06F 3/014; G06F 3/015; G06F 3/017; A61B 5/721; A61B 5/04888; A61B 5/0488
See application file for complete search history.

(56) References Cited

U.S. PATENT DOCUMENTS

2009/0326406 A1*   12/2009   Tan et al. ...................... 600/546
2011/0264238 A1*   10/2011   van der Merwe et al. ...... 623/24

OTHER PUBLICATIONS

Xu Zhang; Xiang Chen; Yun Li; Lantz, V.; Kongqiao Wang; Jihai Yang, "A Framework for Hand Gesture Recognition Based on Accelerometer and EMG Sensors," Systems, Man and Cybernetics, Part A: Systems and Humans, IEEE Transactions on , vol. 41, No. 6, pp. 1064,1076, Nov. 2011.*
Anbin Xiong; Yang Chen; Xingang Zhao; Jianda Han; Guangjun Liu, "A novel HCI based on EMG and IMU," Robotics and Biomimetics (ROBIO), 2011 IEEE International Conference on , vol., no., pp. 2653,2657, Dec. 7-11, 2011.*

* cited by examiner

*Primary Examiner* — James Trammell
*Assistant Examiner* — Adam Mott
(74) *Attorney, Agent, or Firm* — Canady & Lortz LLP; Bradley K. Lortz

(57) ABSTRACT

Systems and methods for sensing human muscle action and gestures in order to control machines or robotic devices are disclosed. One exemplary system employs a tight fitting sleeve worn on a user arm and including a plurality of electromyography (EMG) sensors and at least one inertial measurement unit (IMU). Power, signal processing, and communications electronics may be built into the sleeve and control data may be transmitted wirelessly to the controlled machine or robotic device.

18 Claims, 8 Drawing Sheets

BIOSLEEVE HUMAN-MACHINE INTERFACE

CROSS-REFERENCE TO RELATED APPLICATIONS

This application claims the benefit under 35 U.S.C. §119(e) of the following U.S. provisional patent applications, which are incorporated by reference herein:

U.S. Provisional Patent Application No. 61/651,728, filed May 25, 2012, and entitled "BioSleeve Human-Machine Interface", by Christopher Assad.

STATEMENT OF GOVERNMENT RIGHTS

The invention described herein was made in the performance of work under a NASA contract, and is subject to the provisions of Public Law 96-517 (35 USC 202) in which the Contractor has elected to retain title.

BACKGROUND OF THE INVENTION

1. Field of the Invention

This invention relates to human-machine interfaces. Particularly, this invention relates to human-machine interfaces to control robotic devices.

2. Description of the Related Art

Fundamental to the existence of robotic devices is the requirement for interfaces to facilitate human control of those devices. Robotic devices may include fixed robotic appendages for manipulating objects in space or a factory or mobile robotic units such as unmanned military robots and platforms or cargo manipulators. Some advanced control interfaces have already been developed.

U.S. Pat. No. 8,170,656, issued May 1, 2012 discloses a "Wearable Electromyography-Based Controller" including a plurality of Electromyography (EMG) sensors and provides a wired or wireless human-computer interface (HCI) for interacting with computing systems and attached devices via electrical signals generated by specific movement of the user's muscles. Following initial automated self-calibration and positional localization processes, measurement and interpretation of muscle generated electrical signals is accomplished by sampling signals from the EMG sensors of the Wearable Electromyography-Based Controller. In operation, the Wearable Electromyography-Based Controller is donned by the user and placed into a coarsely approximate position on the surface of the user's skin. Automated cues or instructions are then provided to the user for fine-tuning placement of the Wearable Electromyography-Based Controller. Examples of Wearable Electromyography-Based Controllers include articles of manufacture, such as an armband, wristwatch, or article of clothing having a plurality of integrated EMG-based sensor nodes and associated electronics.

The need for an efficient and reliable means of control is particularly critical in military applications. The current means of unmanned controlling military platforms are not soldier-centric or responsive to the needs of the field personnel. Soldier command of supporting robots and unmanned platforms requires intuitive interfaces to communicate fast, high degree-of-freedom (DOF) information. Command of support robots by the warfighter requires intuitive interfaces to quickly communicate high degree-of-freedom (DOF) information while leaving the hands unencumbered. The need for stealth rules out voice commands and visual gesture interpretation techniques in silent operations at night and/or in low visibility conditions. Any considered robotic military platform should enhance and not inhibit mission performance due to inefficient means of control.

However, the need for efficient systems for controlling machines is not limited to military applications. Any human interface which a user can operate intuitively will enhance overall performance. In addition, intuitive human interfaces can also reduce accidents as the user is able to respond to situations more quickly to dangerous situations when using intuitive interfaces.

In view of the foregoing, there is a need in the art for improved apparatuses and methods for human-machine interfaces in military as well as commercial applications. There is particularly a need for such apparatuses and methods to operate from intuitive action on the part of the user. There is also a need for such systems and methods to function silently and without any visual sensing. Further, there is a need for such interfaces to require only minimal effort by the user (e.g. similar to coordinating with a fellow soldier in a military setting), and ideally such interfaces should employ similar gestures and signals. Further, there is a need for such apparatuses and methods to be simple, efficient, and affordable. These and other needs are met by embodiments of the present invention as detailed hereafter.

SUMMARY OF THE INVENTION

Systems and methods for sensing human muscle action and gestures in order to control machines or robotic devices are disclosed. One exemplary system employs a tight fitting sleeve worn on a user arm and including a plurality of electromyography (EMG) sensors and at least one inertial measurement unit (IMU). Power, signal processing, and communications electronics may be built into the sleeve and control data may be transmitted wirelessly to the controlled machine or robotic device.

A typical embodiment of the invention comprises an apparatus for sensing user input, comprising an elastic material for fitting tightly to a body portion of a user, the body portion having underlying muscles of the user, an array of electromyography (EMG) sensors disposed in the elastic material to be proximate to the underlying muscles of the user in order to sense activity of the underlying muscles and yield EMG electrical signals therefrom, one or more inertial measurement units (IMUs) each disposed on the user for determining position and orientation at each of the one or more inertial measurement units (IMUs) and yielding corresponding IMU data, a processor for receiving the EMG electrical signals and the IMU data and deriving control data for a robotic device, and a power supply powering the signal processor and the one or more IMUs.

In some embodiments, the array of EMG sensors is disposed to exceed an area of the body portion such that only an active subset of the EMG sensors are identified to sense the activity of the underlying muscles and yield the EMG electical signals therefrom. Typically, the EMG electrical signals and the IMU data correspond to static or dynamic gestures of the user. In further embodiments of the invention, the apparatus may further include a wireless transceiver for transmitting the control data to be received by the remote robotic device.

In one exemplary embodiment of the invention, the body portion comprises a forearm of the user and the derived control data corresponds to hand and arm gestures of the user. In this case, the one or more IMUs may comprise a single IMU disposed on a hand of the user. Alternately, the one or more IMUs may comprise two IMUs, one on the forearm and one on a hand of the user. The array of EMG sensors can provide finger position and arm rotation information and the one or more IMUs can provide hand position and arm position information. The finger position and the arm rotation information and the hand position and the arm position information can correspond to static or dynamic gestures of the user.

A typical method embodiment for sensing user input, comprises fitting an elastic material tightly to a body portion of a user, the body portion having underlying muscles of the user, and an array of electromyography (EMG) sensors disposed in the elastic material to be proximate to the underlying muscles of the user, sensing activity of the underlying muscles with the array of EMG sensors to yield EMG electrical signals therefrom, determining position and orientation at each of one or more inertial measurement units (IMUs) each disposed on the user and yielding corresponding IMU data, deriving control data for a robotic device with a processor from the EMG electrical signals and the IMU data, and powering the signal processor and the one or more IMUs with a power supply. This method embodiment of the invention may be further modified consistent with the apparatus embodiments described herein.

Another typical embodiment of the invention may comprise an apparatus for sensing user input, comprising an array of electromyography (EMG) sensors means for sensing activity of underlying muscles of a body portion of a user and yielding EMG electrical signals therefrom, one or more inertial measurement units (IMUs) means for determining position and orientation at each of the one or more inertial measurement units (IMUs), each disposed on the user, and yielding corresponding IMU data, a processor means for deriving control data for a robotic device from the EMG electrical signals and the IMU data, and a power supply means for powering the signal processor and the one or more IMUs. This embodiment of the invention may be further modified consistent with the apparatus or method embodiments described herein.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

Figure 1A:
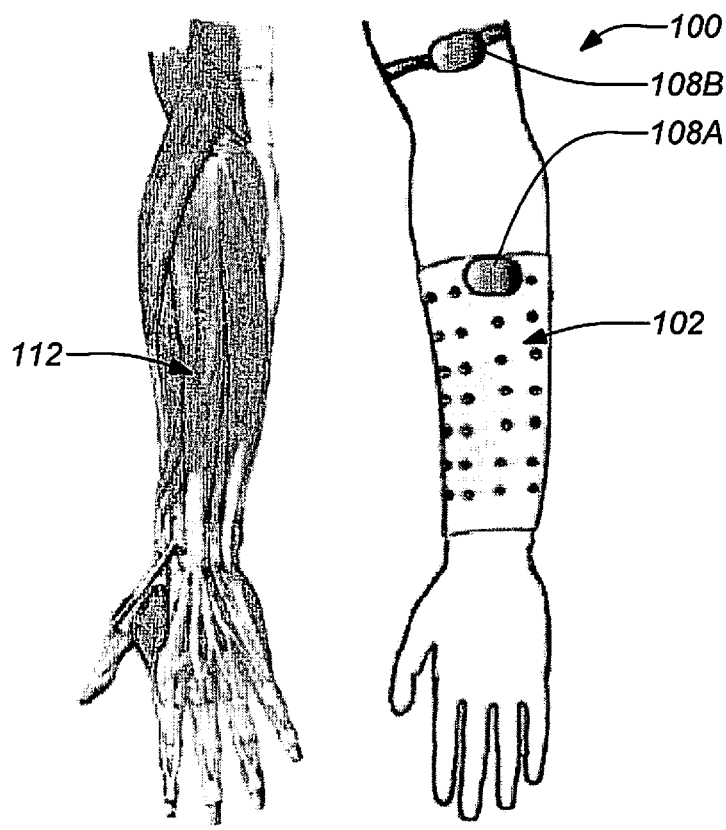
FIGS. 1A and 1B show overall structure and configuration of an exemplary human interface device embodiment of the invention.

Embodiments of the invention may be targeted at using bio-signal inputs to set navigation and manipulation goals for a robot (e.g., simply by pointing). An example system embodiment may comprise an electromyography (EMG) "BioSleeve", having a high density sensor array for robust, practical signal collection from forearm muscles. Significantly, the EMG sensor array data may then be fused with inertial measurement unit (IMU) data to provide enhanced detection of user hand and arm motion.

Embodiments of the invention can be employed to decode robot commands from the EMG and IMU data having up to sixteen bipolar surface EMG sensors in one example. The BioSleeve can be employed in the recognition of static hand positions (e.g. palm facing front, fingers upwards) and dynamic gestures (e.g. hand wave). Embodiments of the invention can achieve over 90% correct recognition in five static and nine dynamic gestures. A BioSleeve embodiment of the invention may be used to control a team of up to five LANdroid robots in individual and group/squad behaviors. A gesture composition mechanism may be defined that allows the specification of complex robot behaviors with only a small vocabulary of gestures/commands that can be illustrated with a set of complex orders.

Embodiments of the present invention are directed to interfaces and control systems that apply biological signals to control robots. Some applications include control of military robotics as well as controlling manipulators in extra-vehicular activity (EVA) activities of spacecraft without having to deal with difficulty of using the EVA suit/gloves.

Electromyogram (EMG) signals are used to provide a direct, higher bandwidth and reliable modality for command interfaces. Applications can also include controlling prosthetic limbs and further, controlling not only one robot with multiple degrees of freedom, but also teams of robots. The interfaces have wide use, from setting navigation and manipulation goals for the robot (say, simply by pointing) to precise control of movement when needed.

Typical embodiments of the invention comprise a wearable sleeve interface ("BioSleeve") for practical signal collection from forearm muscles, incorporating an integrated high density array of surface EMG sensors, several strategically placed inertial sensors, and in-sleeve sensor processing to fuse and decode all signals. One example BioSleeve may include a sensor array of eight to sixteen surface EMG sensors and a six-axis inertial measurement unit (IMU) mounted on the back of the hand.

Implementation of an embodiment of the invention requires overcoming certain technical challenges with surface EMG systems. For example, sensor-to-skin interface issues can cause non-stationarity and signal degradation. In addition, noise and other artifacts from motion of electrodes relative to the skin/muscle can arise with surface EMG systems. Surface EMG systems may also exhibit reliability problems with array packaging. Furthermore, using an array of surface EMG sensors require adequately separating signals that distinguish deeper muscles and individual fingers. Finally, the time-varying stochastic nature of the surface EMG signal itself, particularly for dynamic gestures, must be adequately resolved. Sensor-to-skin and relibility issues are primarily hardware related, whereas noise issues may require a combination of hardware and software refinement. Signal separation and time-varying stochastic issues may be resolved by improved decoding algorithms. EMG data analysis is challenging in general, because the signals are stochastic and noisy, active muscles overlap for various movements, and forearm movements such as twists tend to shift the electrodes with the skin over the underlying muscles. However, studies indicate that individual finger motions and twisting motions of the forearm are distinguishable with enough channels on the forearm.

Conventional EMG electrodes in use today are predominately passive "wet" electrode types with Ag/AgCl adhesive gel interfaces. However, these electrodes can be bothersome to mount and lose signal quality as they dry over time. Dry contact electrodes have also been used, particularly in clinical studies, but they also have interface issues and artifacts from relative motion and require constant mechanical pressure to maintain good skin contact. Practical non-contact sensors are now available, resolving many of these issues. Development of a specific design of an embodiment of the invention requires evaluation of specific sensor performance, including sensitivity to skin-electrode separation distance and saturation from motion artifacts and/or friction-induced electrostatic charge, as will be understood by those skilled in the art. In one example embodiment, conventional electrodes can be employed although the system may be readily adapted to dry or non-contact electrodes.

A variety of references have addressed recognition of EMG signals, but most of the work has focused on a small number of sensors, typically wet contact sensors. In addition, hand and individual finger tracking has been previously demonstrated from small forearm EMG arrays, with the focus on classification of discrete static gestures and not dynamic, temporally varying gestures. In contrast, embodiments of the present invention can classify both static and dynamic gestures.

As detailed hereafter, an example BioSleeve system embodiment of the invention may contain a large dense array of surface EMG sensors, several IMU (MARG) sensors, and onboard processing. The large EMG array allows the user to put it on without needing to make any fine alignment, and so enable the system to be embedded and worn just as clothing. Only a short calibration routine may be required after donning, as well as active channel selection by the onboard processing to find the most informative channels to monitor as many muscles as possible. Furthermore, the system may be packaged into clothing that is elastic and tight fitting, but still comfortable, to ensure consistent pressure on the dry contact or non-contact EMG sensors against the skin. The sensors themselves may be typically constructed of two parts—an amplifier circuit (placed in as close proximity as possible to the electrodes to limit noise), and an electrode that makes contact with the skin. There are several options for the electrode including metal patches such as silver bars, and conductive rubber electrode patches or other conductive textile electrodes and any other suitable electrode type known in the art.

The Biosleeve system can be used to recognize static and dynamic gestures, change input modes, perform gesture control of a small tracked vehicle, telerobotically control a prosthetic hand, and perform point-to-goal and other tele supervision on a semi-autonomous two-armed manipulation robot. The Biosleeve system can be used for many applications including a robotic prosthetics interface, a robotic exoskeleton interface, a power assisted astronaut EVA glove interface, a telerobotic interface. The device may be used in gesture control or to facilitate gesture communications between people—anywhere hand signals are used. In addition, the device may be employed as a computer interface (e.g., virtual mouse and joystick) or force control interfaces. Further, the device may be employed in point-to-goal commanding military fire coordination (e.g., to recognize pointing direction of arm with weapon, recognize when user is firing a weapon). The device may also be employed in sign language recognition and any other application where motion tracking of arm, hand and fingers is useful. Finally, the device may also be employed in health monitoring—e.g. to monitor arm load and muscle fatigue.

Embodiments of the invention employing nonstationary signals can benefit from reliable packaging to reduce artifacts, realtime adaptive pattern recognition software, or periodic recalibration. The elastic material may comprise a stretchable tight fitting garment to hold electrodes consistently on skin. The elastic material (clothing) may be held in place with Velcro, zipper or just pulled on if elasticity is designed correctly. The example sleeve embodiment of the invention may employ low power, low profile sensors and processing built into the sleeve, e.g. with flexible or textile electronics. The processing requires enough analog-to-digital conversion or multiplexing inputs to read all active sensors, to perform real-time processing and classification, and communications (i.e., wireless or USB, etc.) to off board systems acting as the receiver.

2. Exemplary Biosleeve Embodiment of the Invention

This section describes an exemplary embodiment of the invention (e.g. a BioSleeve system), focusing on sensors, data acquisition and the software platform. Exemplary corresponding learning and classification algorithms and their results in the recognition of static and dynamic gestures are presented as well as the use of the gestures to commands and control a group of five robots (e.g. "Landroid" robots).

Figure 1B:
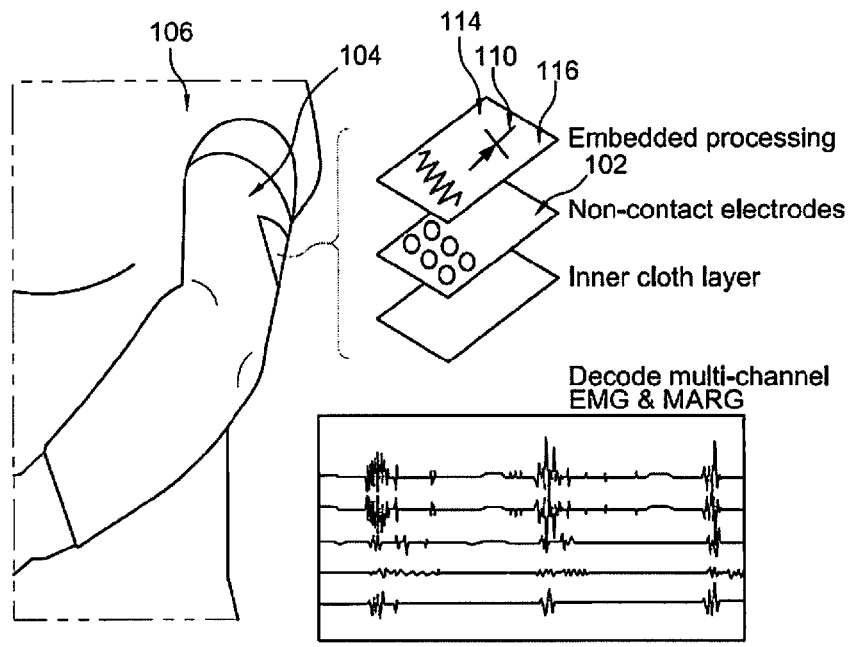

FIGS. 1A and 1B show an exemplary system 100 embodiment of the invention and some of the related concepts. The example system 100 integrates a combination of technologies to enable detailed and accurate arm and hand tracking. An array of EMG sensors 102 are embedded into an elastic material 104 (e.g. a conventional article of clothing or even a single material sleeve worn over just a portion of the body, e.g. an arm or leg) to be unobtrusive to the user 106. The elastic material typically comprises an skin-tight material, e.g., spandex, neoprene or any other suitable material or combination of material layers, capable of holding the EMG sensors 102 close enough to the users underlying muscles 112 to detect electromagnetic signals corresponding to muscle activity. The elastic material 104 fits tightly to a body portion of the user having underlying muscles such that the array of electromyography (EMG) sensors are disposed in the elastic material to be proximate to the underlying muscles of the user in order to sense activity of the underlying muscles and yield EMG electical signals therefrom. Although embodiments of the invention may be developed to operate with any body portion having relevant underlying muscles, typically the body portion may comprise the forearm. In this case, the activity of the forearm muscles can be directly correlated to hand positions and gestures.

Further embodiments of the invention may also be developed to manipulate robotic limbs for amputees. The elastic material having the array of embedded EMG sensors is typically structured to fit over the residual muscles on the limb. In some applications, motor nerves projecting to muscle tissue formerly associated with the amputated limb may be transplanted, e.g. to muscle tissue in the upper chest, shoulder, etc. The elastic material having the array of embedded EMG sensors is appropriately structured to fit over the reinnervated muscle tissue area. Operation by the user is facilitated in this manner because the user still "feels" he is moving the missing limb.

Compact low power IMU sensors, e.g. employing MEMS technology, have been developed in recent years for determining position, orientation (as well as velocity and acceleration) at their mounted location. Typcially, IMUs provide angular velocity and linear acceleration information that must be numerically integrated to give position data as part of the processing. Accelerometer outputs of IMUs also indicate the direction of the gravity vector. In addition, the addition of a three-axis magnetic field sensor can give orientation with respect to the Earth's magnetic field and help correct for offsets in the IMU integration. One example IMU suitable for use with embodiments of the invention delivers nine axes—three for gyrometers, three for accelerometers, and three for magnetic field vector. (Note that IMUs of this type may be alternately referenced as a MARG for magnetic, angular rat and gravity, however, as used herein, the term IMU includes a MARG sensors.) MARG sensors can aid with tracking absolute orientation with respect to Earth's magnetic field, so they can be used as a magnetic compass, help calculate a pointing vector, and help correct for bias and drifts in the IMU integration.

Another example embodiment of the invention may use of up to four IMU (MARG) sensors in the Biosleeve device—one on shoulder, upper arm, forearm, and hand. The differences between the signals from the different body locations allow computation of relative position and velocities, e.g. of arm and hand with respect to the body. This allows the system to compute arm posture for example. If the user is also tracked in space (e.g., with GPS or other suitable tracking device) then an absolute pointing vector may also be calculated to enable point-to-goal commands and other relationships with external objects/robots, etc. The use of IMU (MARG) (e.g., pointing the arm straight up) or EMG signals (e.g., a hand squeeze) may also be employed to signal command initiation/verification, or to signal change of modes so that the device can change its robotic target or command dictionary. The IMU (MARG) sensors can also be used to correct for EMG signal variation due to pose (e.g., the EMG pattern may differ for the same hand gesture in two different arm poses, due to the need to oppose a different gravity vector).

One or more such inertial measurement unit (IMU) sensors 108A, 108B are also used to estimate limb position and orientation with respect to the body. Each IMU 108A, 108B is disposed on a separately moving portion of the user body in order to sense differential movement between the body parts. For example, one IMU 108A may be disposed on the forearm and another IMU 108B disposed on the upper arm. (Optionally, a third IMU 108C may also be disposed on the torso to establish a reference relative to arm position. Alternately, in some applications sufficient position data may be derived from a single IMU 108D disposed on the hand, forearm, or upper arm.) The IMU sensors 108A-108D may be any known suitable compact, low power IMU device capable of delivering data to the device processor.

The processor 110 and power supply 114 which include advanced decoding algorithms for gesture recognition may also be embedded in the elastic material 104. The built-in power supply 114 is used to power the EMG sensors 102 (which may alternately be passive sensors), one or more IMUs 108A-108D, and processor 110 as necessary. The processor (or circuit) 110 for receiving the EMG electrical signals and the IMU data and deriving control data for a robotic device may comprise a single unit, but more likely will include multiple separate components coupled together as will be understood by those skilled in the art. Optionally, the device 100 may also include a wireless transceiver 116 for transmitting the control data to be received by a remote robotic device.

Figure 1C:
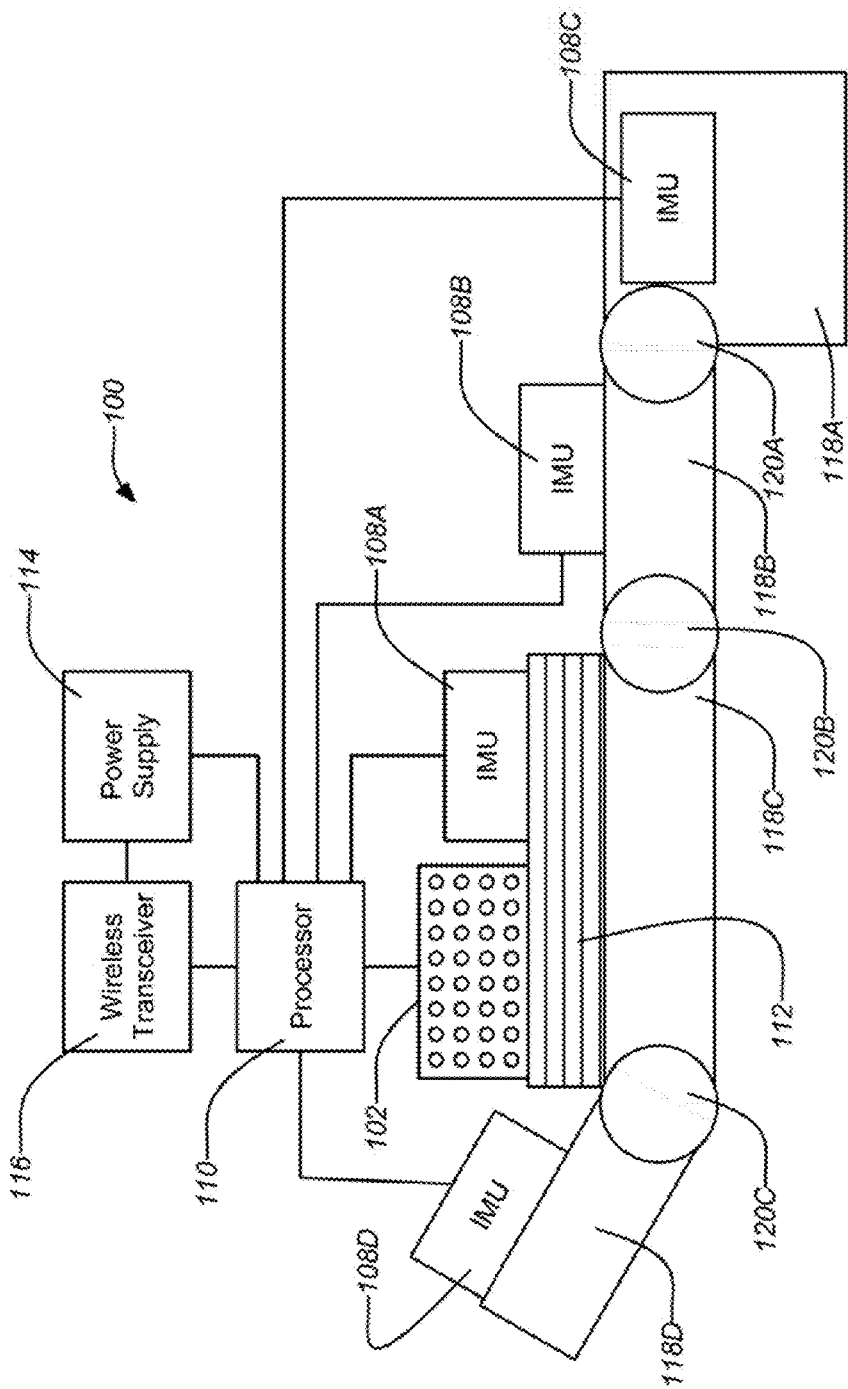
FIG. 1C is a schematic diagram of system architecture of the exemplary human interface device embodiment of the invention.

FIG. 1C is a schematic diagram of the system 100 of the exemplary human interface device embodiment of the invention. Different portions of the user 106 body are shown schematically including a torso 118A, upper arm 118B, forearm 118C and hand 118D separated by the individually joint 120A-120C. (Note that individual fingers of the hand are not shown.) The system 100 combines an array of EMG sensors 102 and an IMU sensor 108A both disposed on the forearm 118C of a user 106. It is known that activity of the muscles 112 of the forearm 118C can be correlated to gestures of the hand 118D including individual finger positions. The array of EMG sensors 102 operate to detect this muscle 112 activity and generate signals which can then be interpreted by a processor 110 to identify a gesture of the hand 118D (a specific combination of finger positions or motions). As previously mentioned, the array of EMG sensors 102 are embedded in an elastic material 104 (previously shown in FIGS. 1A and 1B) so that it can be simply worn by the user 106 to operate. In one basic example, the elastic material 104 comprises an elastic sleeve similar to athletic support sleeves. In some embodiments the elastic material 104 may comprise merely an elastic material band (i.e. an extremely shortened "sleeve"). This is operable because the only a short semi-circumferential area is necessary to capture much the pertinent muscle activity in the arm which corresponds to hand position.

An important feature of the system 100 is the use of an excess of EMG sensors in array to cover an area larger than would otherwise be necessary to sufficiently detect the pertinent muscle activity. This is to avoid the need for precise physical alignment of the EMG sensors by the user. The user 106 need only position the elastic material 104 (e.g. clothing) roughly over the proper muscles 112. Calibration of the system 100 may then be performed electronically and automatically. As the user performs gestures, the array of EMG sensors 102 are monitored and the properly positioned EMG sensors of the array may then be isolated in the array based on their responses.

Those skilled in the art will appreciate that inventive concept is not limited to arm and hand motion/position input, but may be readily applied to any moving portion of the body suitable for a particular application. For example, in further embodiments, the BioSleeve system 100 can be expanded to two arms including measurement of all degrees of freedom, to estimate position and orientation of carried equipment, and/or adding wearable sensors to monitor leg, head, and body posture (i.e., in a "BioSuit").

Figure 2A:
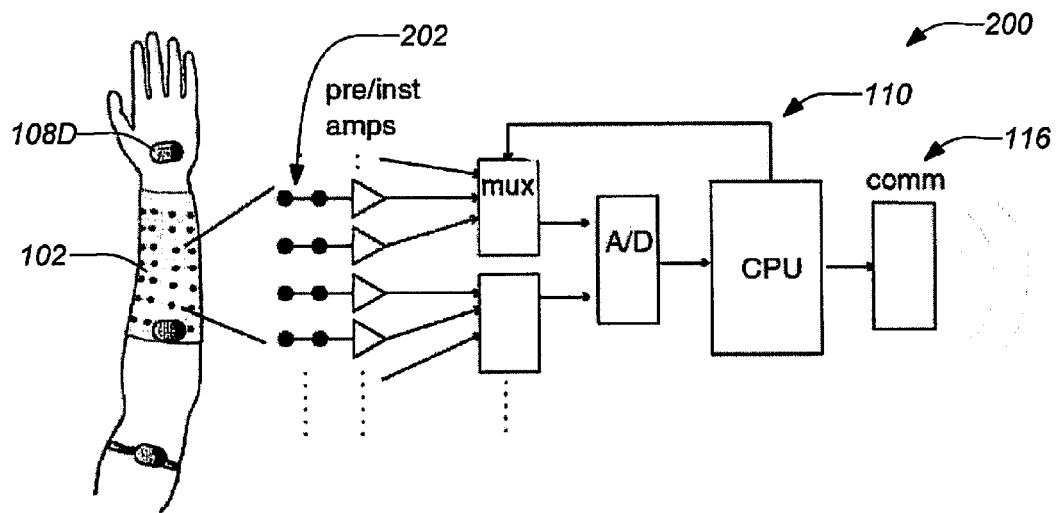
FIG. 2A is a schematic diagram of an exemplary embodiment of the invention comprising an array of bipolar surface EMG sensors and a plurality of IMUs.
Figure 2B:
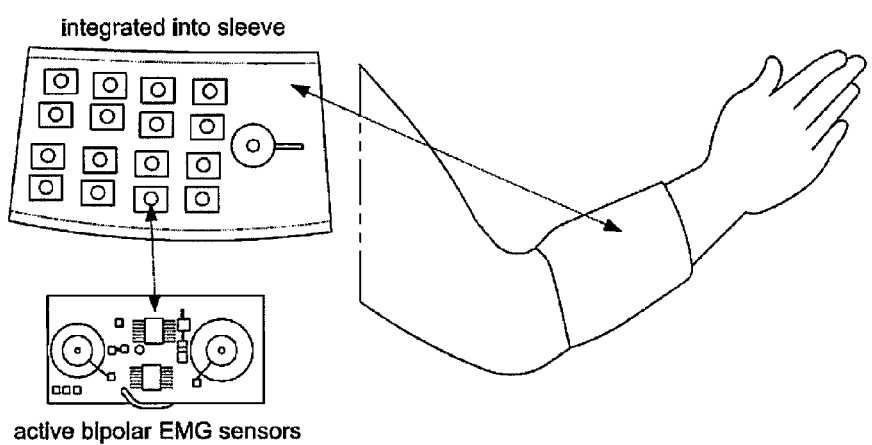
FIG. 2B shows an exemplary array of bipolar surface EMG sensors embedded in a forearm sleeve of elastic material.

FIG. 2 shows an exemplary device 200 embodiment of the invention comprising an array of bipolar surface EMG sensors 102 embedded in a forearm sleeve of elastic material 104, with a single IMU 108D worn on the hand 118D. A small, low power, differential EMG amplifier circuit may be integrated into the sleeve. The circuit may be based around a surface mount instrumentation amplifier (INA321 from Texas Instruments), analog bandpass filtering and output buffer, and snap buttons for electrode attachment as will be understood by those skilled in the art. The snaps may be soldered onto the amplifier board, and aligned with holes in the sleeve material, through which disposable clinical wet electrodes are snapped in. An array of these circuits can fit into an elastic sleeve material for mounting on the user's forearm 118C. Using the example circuit, the EMG signals may be amplified, bandpass filtered, and buffered, and then transmitted through a wire tether 202 to an off-board processor 110 for digitization (which may disposed remotely elsewhere on the user, e.g. in a clothing pocket or pouch) and processing to yield the control data for the robotic device. A wireless transceiver 116 may be use to communicate the derived control data to the robotic device. The example circuit characteristics may include power input of 228 μW (76 μA at 3V) during operation and less than 5 μA in sleep mode, gain of 100 V/V and frequency pass band of 16 to 600 Hz.

Figure 3A:
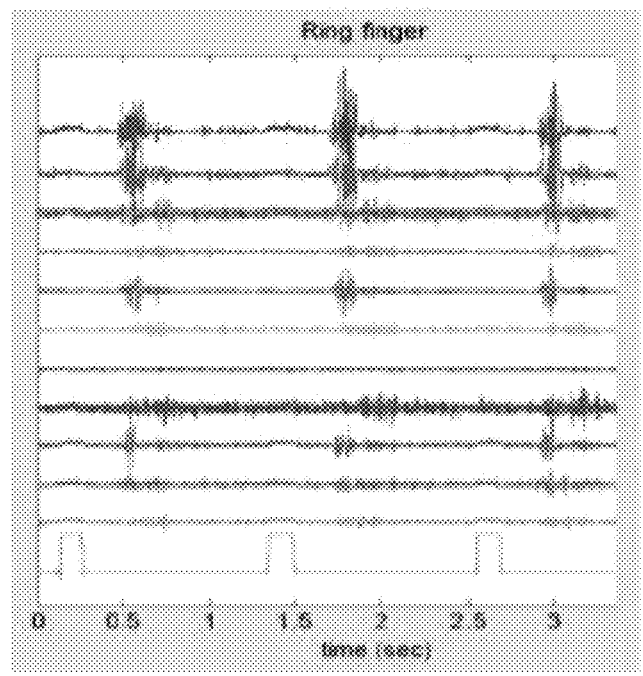
FIG. 3A shows an example of raw EMG sensor data captured from an array of sensors on a forearm sleeve due to individual finger motion of the ring finger.
Figure 3B:
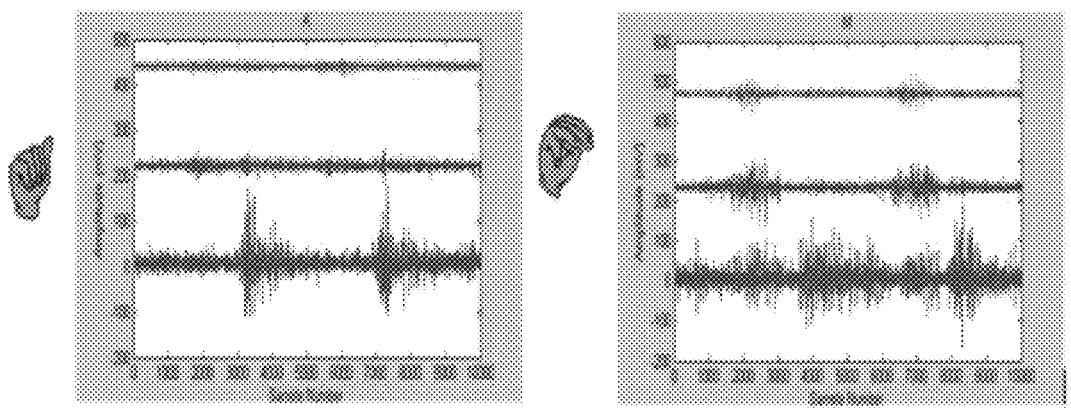
FIG. 3B shows sample raw EMG sensor data corresponding to two similar letters (A and M) of the American Sign Language alphabet.

FIG. 3 shows some example raw EMG signals from an exemplary system embodiment of the invention. Embodiments of the invention may be implemented with either wet clinical electrodes or dry (i.e., no contact gel) electrodes in elastic skin-tight sleeves. Using the wet adhesive electrodes may make the sleeve/sensor array more difficult to mount. Dry electrodes have a potential advantage in ease of use for mounting the BioSleeve system on the user's arm, but may have lower signal to noise ratio if not in good skin contact. The sensors require constant mechanical pressure to maintain good skin contact. Accordingly, a skin-tight properly sized material garment or sleeve is important. A system with sixteen channels of bipolar sensor circuits for the in-sleeve array can be implemented. As previously discussed, embodiments of the invention can benefit from an oversized array of EMG sensors to avoid tedious sensor positioning and calibration. The array of EMG sensors need only be placed over the relevant muscle area and the EMG sensors of the array which happen to be over the proper muscles are selectively monitored.

Packaging the array in elastic sleeve materials proved to be the major challenge for reliability, because breaks in the array wiring from motion caused most experiments to be run with twelve or fewer working channels. One basic embodiment may use eight bipolar sensors with two wet adhesive electrodes per sensor. However, an improved embodiment of the invention may use commercial bipolar sensors with two silver bar electrodes per sensor.

3. Example Gesture Recognition with Biosleeve Human-Machine Interface

The signals acquired and filtered by human-interface embodiments of the invention may be sent off-board for gesture recognition processing. In some implementations, static gestures may be classified using the EMG signals in a Support Vector Machine (SVM) algorithm and dynamic gestures may use IMU data in a custom technique founded on a spatial pattern recognition/dynamic programming technique. Further embodiments of the invention can integrate both EMG and IMU signals for both types of gestures. After donning the device, the user can complete a quick 2-5 minute calibration exercise, which collects data in each gesture to train the classifiers.

In some embodiments, static gestures may be implemented to enable a "virtual joystick" with five basic commands: left, right, forward, backward, and stop. These commands may be accomplished with hand position only (allowing any arm position/orientation) and thus required only EMG signals. The classification approach may be founded on multiclass SVM, which reduces the single multiclass problem into multiple binary classification problems. For example, a five-class SVM may be applied to an eight-channel EMG feature vector, where a feature is defined as the standard deviation of the EMG amplitude over the last 0.5-second window. One challenge of using amplitude-based signals, however, is that they can vary as the battery voltage supplied to the device decreases. Compensation for this effect can be effected in software by offsetting the feature vector by the minimum value of the vector.

The classification algorithms and command interfaces for use with an embodiment of the invention may also be implemented on an off-board computer (although this is less desirable than implementation on-board the device as previously described), which then sends the interpreted commands to the controlled robotic device, e.g. in on example, up to five LANdroid mobile robots (iRobot Corp., USA) in real time.

Figure 4:
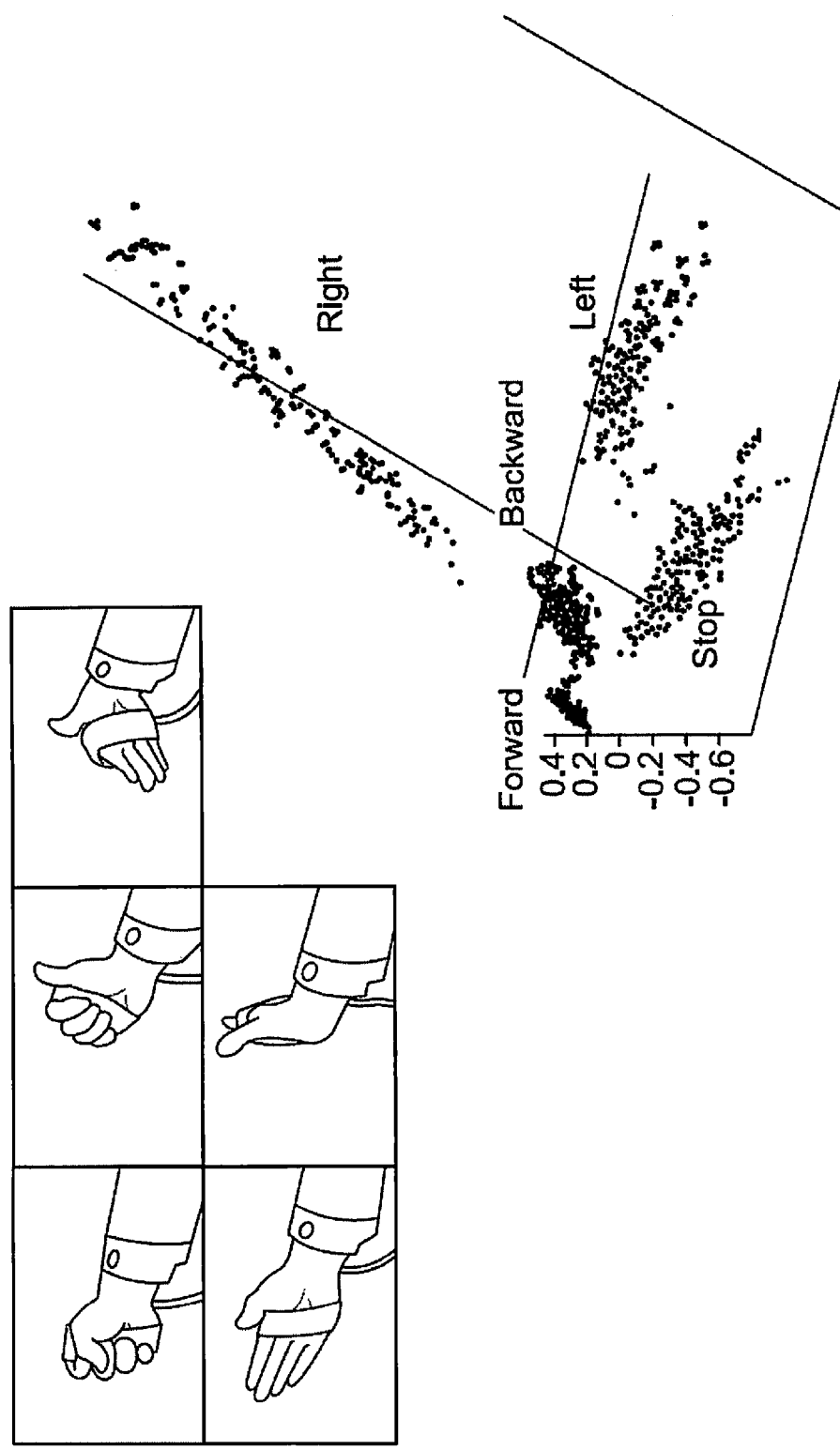
FIG. 4 shows the example five basic static gestures and their corresponding EMG signals displayed in their three-dimensional pricipal components.

FIG. 4 illustrates the labeled EMG data for the five static gestures. The separability of the gesture classes indicates the device can provide high signal quality and data that is valuable for detecting the user's finger position (i.e. hand shape). The gesture classes can then be mapped to commands sent to one or more robotic devices, so the user can direct the robotic device with these hand shapes. Classification accuracy can be consistently over 90%, with some tests indicating virtually 100% accuracy (over 600 consecutive time steps), although these results may be limited to a single user operating within about 30 minutes of calibration.

To classify dynamic gestures, patterns of feature vector changes over time need to be detected and extracted. Dynamic programming (DP) can be used in the analysis, as it was previously successfully demonstrated for gesture recognition due to its ability to optimally compensate for nonlinear time fluctuations of gestures. During training and testing recognition the movements can be repeated a number of times.

Figure 5A:
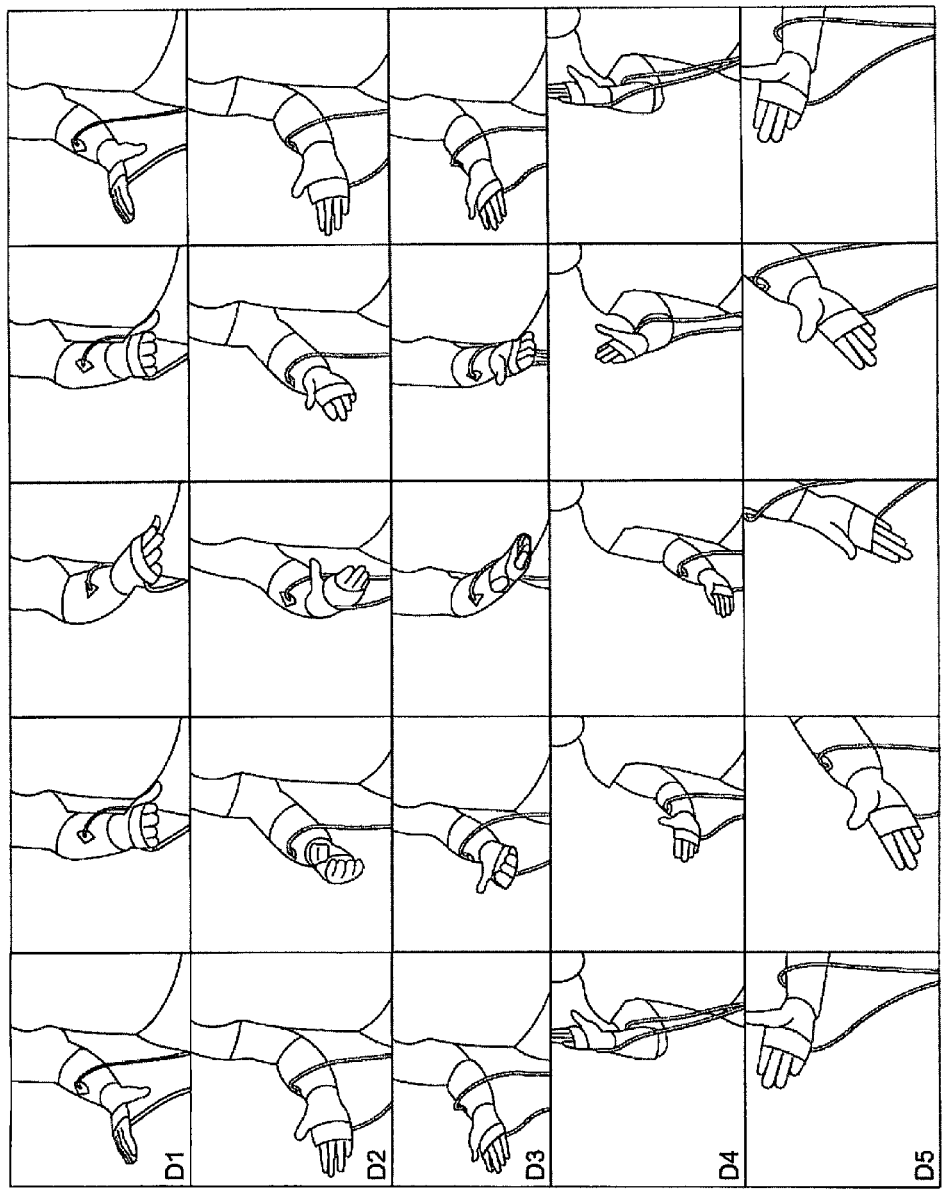
FIGS. 5A and 5B show nine different dynamic gestures (D1 to D9) which can be captured combining EMG and IMU sensor data.
Figure 5B:
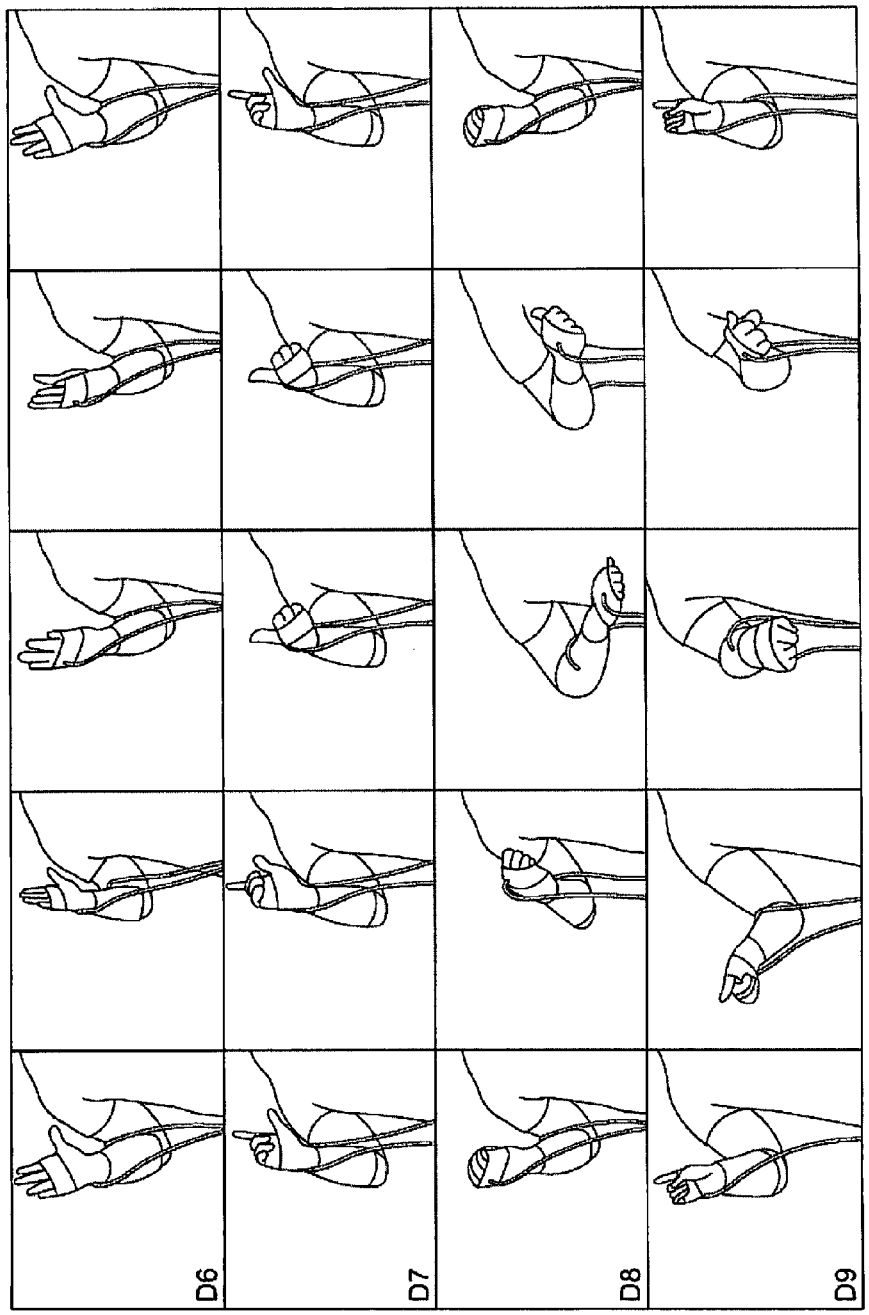

FIGS. 5A and 5B show nine different dynamic gestures (D1 to D9) which can be captured combining EMG and IMU sensor data to reflect gestures involving motion of the fingers and arm (including hand). Five significant frames are shown for each dynamic gesture (D1 to D9) over a complete period, or hand/arm movement return to the starting position (which may not be needed for all gestures). Typically, the array of EMG sensors provides finger position and arm rotation information and the one or more IMUs provide hand position and arm position information. In addition, the EMG array and IMUs are now used to detect dynamic movements of the fingers and arm as gestures.

Although the system should be calibrated to the user for optimal results, the system will generalize well to any user because of the similarities in anatomy of the human arm and muscles. EMG data analysis for detailed gestures and hand/finger poses may be more challenging, because the signals are stochastic and noisy, active muscles overlap for various movements (many to many mapping between muscles and fingers), and forearm movements such as twist tend to shift the electrodes with the skin over the underlying muscles. However, detailed gesture sensing readily achievable employing an embodiment of the invention as will be understood by those skilled in the art.

Collecting simultaneous EMG data from the forearm employing an embodiment of the invention with a sufficient density of EMG sensors in the array and active channel selection, one can distinguish patterns of muscle activities underlying different hand and finger motions, including individual finger motions and twisting motions of the forearm. This discrimination capability will be particularly important for correct classification between two similar hand/finger configurations, such as those shown in FIGS. 3A and 3B.

4. Exemplary Method of Sensing User Input

Figure 6:
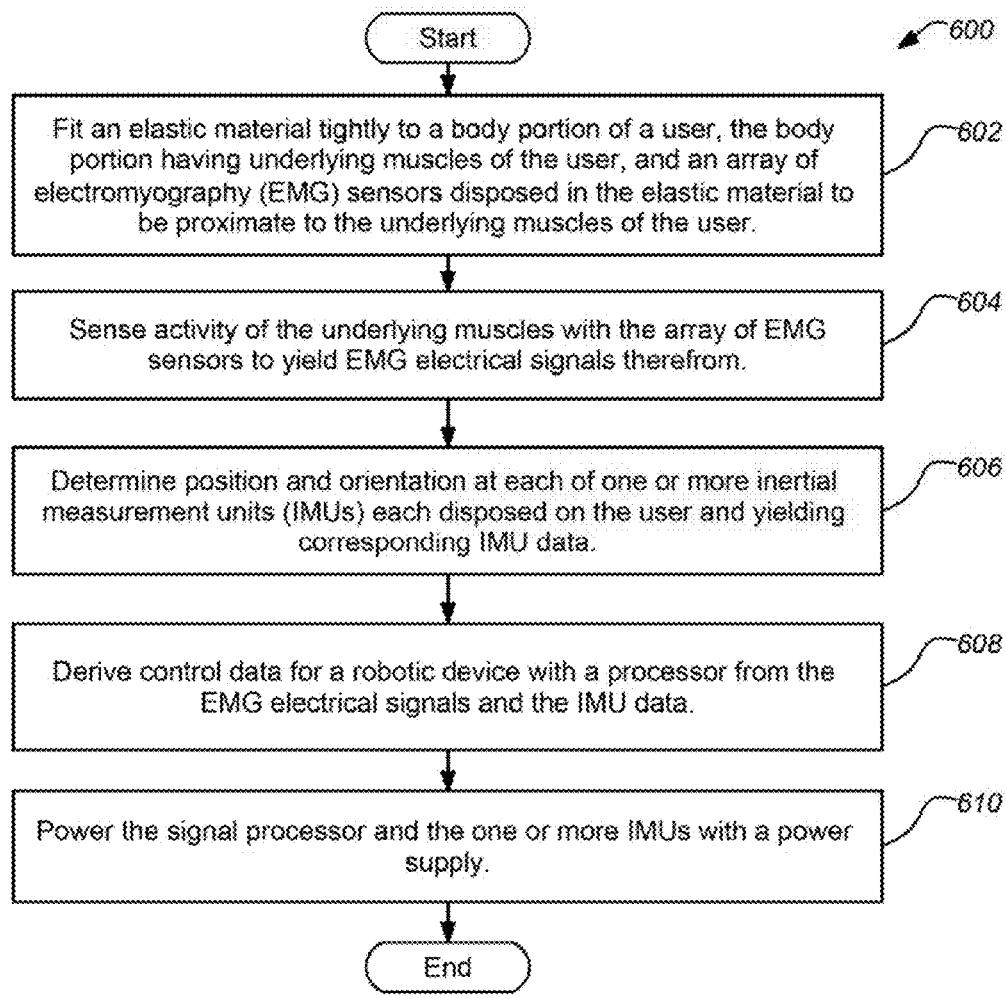
FIG. 6 is a flowchart of an exemplary method of sensing user input.

FIG. 6 is a flowchart of an exemplary method 600 of sensing user input. The method 600 includes an operation 602 of fitting an elastic material tightly to a body portion of a user, the body portion having underlying muscles of the user, and an array of electromyography (EMG) sensors disposed in the elastic material to be proximate to the underlying muscles of the user. Next in operation 604, activity of the underlying muscles is sense with the array of EMG sensors to yield EMG electrical signals therefrom. In operation 606, position and orientation at each of one or more inertial measurement units (IMUs) is determined, each disposed on the user, and corresponding IMU data is yielded. In operation 608, control data is derived for a robotic device with a processor from the EMG electrical signals and the IMU data. In operation 610, the signal processor and the one or more IMUs are powered with a power supply.

This method 600 may be altered consistent with the various apparatus embodiments previously described. For example, some embodiments may include the additional operation of transmitting the control data to be received by the remote robotic device with a wireless transceiver. It is important to also note that the steps may be performed in any suitable order (or simultaneously) as will be appreciated by those skilled in the art.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. An apparatus for sensing user input, comprising:
    an elastic material for fitting tightly to a body portion of a user, the body portion having underlying muscles of the user;
    an array of electromyography (EMG) sensors disposed in the elastic material to be proximate to the underlying muscles of the user in order to sense activity of the underlying muscles and yield EMG electrical signals therefrom;
    a plurality of inertial measurement units (IMUs) each disposed on a separately moving portion of the user for determining position and orientation of each of the plurality of inertial measurement units (IMUs) in order to sense differential movement between body parts and yielding corresponding IMU data, each IMU providing nine-axis measurements, three for gyrometers, three for accelerometers and three for magnetic field vector;
    a processor for receiving the EMG electrical signals and the IMU data and deriving control data for a robotic device; and
    a power supply powering the processor and the plurality of IMUs.

2. The apparatus of claim 1, wherein the array of EMG sensors is disposed to exceed an area of the body portion such that only an active subset of the EMG sensors are identified to sense the activity of the underlying muscles and yield the EMG electrical signals therefrom.

3. The apparatus of claim 1, wherein the EMG electrical signals and the IMU data correspond to static or dynamic gestures of the user.

4. The apparatus of claim 1, further comprising a wireless transceiver for transmitting the control data to be received by the remote robotic device.

5. The apparatus of claim 1, wherein the body portion comprises a forearm of the user and the derived control data corresponds to hand and arm gestures of the user.

6. The apparatus of claim 5, wherein the plurality of IMUs comprise three IMUs, one on a forearm of the user, one on an upper arm of the user, and one on the torso of the user.

7. The apparatus of claim 5, wherein the array of EMG sensors provides finger position and arm rotation information and the one or more IMUs provide hand position and arm position information.

8. The apparatus of claim 7, wherein the finger position and the arm rotation information and the hand position and the arm position information correspond to static or dynamic gestures of the user.

9. A method for sensing user input, comprising:
    fitting an elastic material tightly to a body portion of a user, the body portion having underlying muscles of the user, and an array of electromyography (EMG) sensors disposed in the elastic material to be proximate to the underlying muscles of the user;
    sensing activity of the underlying muscles with the array of EMG sensors to yield EMG electrical signals therefrom;
    determining position and orientation of each of a plurality of inertial measurement units (IMUs) each disposed on a separately moving portion of the user in order to sense differential movement between body parts and yielding corresponding IMU data each IMU providing nine-axis measurements, three for gyrometers, three for accelerometers and three for magnetic field vector;
    deriving control data for a robotic device with a processor from the EMG electrical signals and the IMU data; and
    powering the processor and the one or more IMUs with a power supply.

10. The method of claim 9, wherein the array of EMG sensors is disposed to exceed an area of the body portion such that only an active subset of the EMG sensors are identified to sense the activity of the underlying muscles and yield the EMG electrical signals therefrom.

11. The method of claim 9, wherein the EMG electrical signals and the IMU data correspond to static or dynamic gestures of the user.

12. The method of claim 9, further comprising transmitting the control data to be received by the robotic device with a wireless transceiver.

13. The method of claim 9, wherein the body portion comprises a forearm of the user and the derived control data corresponds to hand and arm gestures of the user.

14. The method of claim 13, wherein the plurality of IMUs comprise three IMUs, one on a forearm of the user, one on an upper arm of the user, and one on the torso of the user.

15. The method of claim 13, wherein the array of EMG sensors provides finger position and arm rotation information and the plurality of IMUs provide hand position and arm position information.

16. The method of claim 15, wherein the finger position and the arm rotation information and the hand position and the arm position information correspond to static or dynamic gestures of the user.

17. An apparatus for sensing user input, comprising:
    a plurality of muscle activity sensing means for sensing activity of underlying muscles of a body portion of a user and yielding electrical signals therefrom, the plurality of sensor means disposed in an array;
    a plurality of inertial sensing means for determining position and orientation of each of the plurality of inertial sensing means, each inertial sensing means disposed on a separately moving portion of the user, in order to sense differential movement between body parts and yielding corresponding inertial data, each inertial sensing means providing nine-axis measurements, three for gyrometers, three for accelerometers and three for magnetic field vector;

a processing means for deriving control data for a robotic device from the electrical signals and the inertial data; and a supply means for powering the processing means and the plurality of inertial sensing means.

18. The apparatus of claim 17, wherein the array of muscle activity sensing means is disposed to exceed an area of the body portion such that only an active subset of the muscle activity sensing means are identified to sense the activity of the underlying muscles and yield the electrical signals therefrom.

* * * * *